(12) United States Patent
Racenet

(10) Patent No.: US 10,278,698 B2
(45) Date of Patent: May 7, 2019

(54) CONTROLLED TISSUE COMPRESSION SYSTEMS AND METHODS

(71) Applicant: Covidien LP, Mansfield, MA (US)

(72) Inventor: David C. Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/828,895

(22) Filed: Dec. 1, 2017

(65) Prior Publication Data

US 2018/0085121 A1      Mar. 29, 2018

Related U.S. Application Data

(63) Continuation of application No. 13/346,954, filed on Jan. 10, 2012, now abandoned.

(60) Provisional application No. 61/445,700, filed on Feb. 23, 2011.

(51) Int. Cl.
*A61B 17/072* (2006.01)
*A61B 17/00* (2006.01)
*A61B 90/00* (2016.01)

(52) U.S. Cl.
CPC ............ *A61B 17/07207* (2013.01); *A61B 2017/00022* (2013.01); *A61B 2017/00039* (2013.01); *A61B 2017/00137* (2013.01); *A61B 2017/00154* (2013.01); *A61B 2017/00398* (2013.01); *A61B 2090/061* (2016.02); *A61B 2090/065* (2016.02); *A61B 2090/066* (2016.02)

(58) Field of Classification Search
CPC ........ A61B 17/07207; A61B 2090/061; A61B 2090/065; A61B 2017/00022; A61B 2017/00039; A61B 2017/00137; A61B 2017/00154; A61B 2017/00398
USPC ............................................. 227/175.1, 176.1
See application file for complete search history.

(56) References Cited

U.S. PATENT DOCUMENTS

| 5,383,880 | A | | 1/1995 | Hooven |
| 5,667,517 | A | * | 9/1997 | Hooven ............... A61B 17/072 227/175.1 |
| 5,810,811 | A | | 9/1998 | Yates et al. |
| 7,032,798 | B2 | | 4/2006 | Whitman et al. |
| 8,012,170 | B2 | | 9/2011 | Whitman et al. |
| 8,808,311 | B2 | | 8/2014 | Heinrich et al. |
| 2004/0153124 | A1 | | 8/2004 | Whitman |
| 2008/0251568 | A1 | | 10/2008 | Zemlok et al. |
| 2008/0272172 | A1 | | 11/2008 | Zemlok et al. |

(Continued)

FOREIGN PATENT DOCUMENTS

| EP | 2027819 A1 | 2/2009 |
| EP | 2245994 A1 | 11/2010 |

OTHER PUBLICATIONS

European Search Report dated Feb. 12, 2015, issued in European Application No. 12190101.

(Continued)

*Primary Examiner* — Michelle Lopez

(57) ABSTRACT

A surgical instrument is provided including an end effector configured to clamp, staple or cut tissue, a motor configured to drive the end effector and a control system. The control system is configured to receive information about at least one tissue property and select a tissue management mode based on the at least one tissue property. The control system controls the motor based on the selected tissue management mode.

18 Claims, 3 Drawing Sheets

(56) References Cited

U.S. PATENT DOCUMENTS

| | | |
|---|---|---|
| 2009/0012556 A1 | 1/2009 | Boudreaux et al. |
| 2009/0057369 A1 | 3/2009 | Smith et al. |
| 2009/0090763 A1 | 4/2009 | Zemlok et al. |
| 2009/0108048 A1 | 4/2009 | Zemlok et al. |
| 2009/0112271 A1 | 4/2009 | Moskowitz et al. |
| 2010/0133318 A1 | 6/2010 | Boudreaux |
| 2010/0270355 A1* | 10/2010 | Whitman ............. A61B 17/068 227/176.1 |
| 2011/0017801 A1 | 1/2011 | Zemlok et al. |
| 2011/0125138 A1 | 5/2011 | Malinouskas et al. |
| 2012/0211542 A1 | 8/2012 | Racenet |

OTHER PUBLICATIONS

European Search Report dated Jul. 3, 2012, corresponding to European Application No. 12156454; 10 pages.

* cited by examiner

CONTROLLED TISSUE COMPRESSION SYSTEMS AND METHODS

CROSS-REFERENCE TO RELATED APPLICATIONS

The present application is a Continuation Application of U.S. patent application Ser. No. 13/346,954, filed on Jan. 10, 2012, which claims the benefit of and priority to U.S. Provisional Application Ser. No. 61/445,700, filed on Feb. 23, 2011, the entire contents of each of which are incorporated herein by reference.

BACKGROUND

1. Technical Field

The present disclosure relates generally to medical devices. More specifically, the present disclosure relates generally to systems and methods for controlled tissue compression.

2. Background of the Related Art

Some surgical procedures require the compression, e.g., clamping, of a patient's tissue. Such procedures may include, e.g., anastomosing, stapling, and resecting of tissue. For example, where cancerous tissue is identified in a patient's gastrointestinal tract, the cancerous tissue may need to be surgically removed. Where, for example, the cancerous tissue is located on the colon and is accessible by surgical instrumentation, the surgeon may make an incision in the patient's abdomen to allow access to the bowel. The surgeon may then use a linear cutting and stapling device, such as that described in U.S. patent application Ser. No. 12/235,362, filed Sep. 22, 2008 (U.S. Pat. No. 7,963,433), which is expressly incorporated herein in its entirety by reference thereto, to cut and staple the colon tissue on opposite sides of the cancerous portion to be removed. In this procedure, the colon is externally clamped (e.g., between opposed jaws) to compress the tissue. While the tissue is compressed, a cutter and a stapler are activated to make a linear cut and apply typically two linear rows of staples in the areas adjacent the cut. The stapling thus closes both open ends of the portion of the bowel to be removed, as well as providing a temporary closure of the two cut ends of the bowel. This closure limits exposure of the surrounding tissue to the interior of the bowel, thus limiting the risk of infection. After the cutting and stapling procedure, the cancerous portion of tissue may be removed from the patient's body.

After the resection of the cancerous tissue, the surgeon may employ an anastomosing and stapling device, e.g., a circular stapler/cutter, such as that described in U.S. patent application Ser. No. 10/785,682, filed Feb. 24, 2004 (U.S. Pat. No. 7,342,983), which is expressly incorporated herein in its entirety by reference thereto. During this procedure a head portion is positioned within the colon adjacent one of the cut ends and a base or shaft portion is positioned within the colon adjacent the other cut end. The head portion and the base portion may be coupled via a shaft and/or cable that extends out of one cut end and into the other. Via this coupling, the surgeon is able to actuate the anastomosing and stapling device to draw the head portion and the base portion together. After the two cut ends of the colon contact each other, the actuation continues such that the two portions of the colon are clamped together at an annular area of contact. While clamped, the anastomosing and stapling device may be further actuated to apply an annular ring of staples into the compressed tissue. The device may also cut excess tissue disposed within the colon. The head portion and the base portion are then moved apart and the anastomosing and stapling device removed from the patient.

To achieve effective stapling in the above procedures, the tissue must be compressed to the extent that there is an adequately small tissue gap, e.g., one millimeter, between the faces of the tool. If the clamping structures of the instrument are exposed to enough force, maintaining a uniform target tissue gap across the length of tissue to be stapled may be difficult or even impossible.

Moreover, when performing the compression, a constant closing rate (e.g., the closing rate between jaws of a linear stapler or between the head and base portion of a circular stapler/cutter) may exert a high level of power into the clamped tissue. This high level of power may result in excess tissue trauma. It is thus desirable to limit this trauma, e.g., by effectively controlling the power applied to the tissue.

Further, it is desirable to determine how the tissue to be clamped is responding to compression and process this information to determine clamping pressure. U.S. patent application Ser. No. 09/510,927, filed Feb. 22, 2000 (now U.S. Pat. No. 6,716,233), which is expressly incorporated herein in its entirety by reference hereto, describes apparatus and methods of using a tissue sensor to control operation of a surgical stapler.

SUMMARY

In an embodiment of the present disclosure, a surgical device is provided. The surgical device includes an end effector configured to clamp, staple or cut tissue, a motor configured to drive the end effector and a control system. The control system receives information about at least one tissue property and selects a tissue management mode based on the at least one tissue property. The control system controls the motor based on the selected tissue management mode.

The surgical device may also include an indicator that provides a clinician with a status of a tissue gap range of the end effector and a sensor array configured to detect at least one tissue property. The sensor array detects at least one tissue property by measuring the current draw on the motor or the dwell effect at the end effector.

The tissue management modes that can be selected by the surgical device include a constant torque profile, a modulated torque profile, a maximum torque profile or a manual override mode. The control system applies a constant signal to the motor in the constant torque profile or a periodic signal to the motor in the modulated torque profile. In the maximum torque profile, the powered surgical instrument fires at a speed that is faster than the speed of firing in the constant torque profile, the modulated torque profile or the manual override mode. In the manual override mode, the user manually controls the motor.

In another embodiment of the present disclosure, a method for applying a staple by a powered surgical instrument is provided. The method includes the steps of providing a surgical instrument having an end effector that is powered by a motor, inputting a tissue type and/or disease type, clamping tissue using the end effector driven by the motor, detecting at least one tissue property of the clamped tissue, determining if a desired tissue gap range is achieved by the end effector, selecting a tissue management mode to apply to clamp tissue to achieve the desired tissue gap, and firing the powered surgical instrument in the selected tissue management mode to apply staples to the clamped tissue.

The method may also include the step of providing an indication of a status of a tissue gap range. The tissue property may be detected by measuring the current draw on the motor or measuring a dwell effect at the end effector.

Selecting the tissue management mode may be based on the tissue property of the clamped tissue detected or be performed by a clinician. The tissue management modes that can be selected by the surgical device include a constant torque profile, modulated torque profile, maximum torque profile or a manual override mode.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
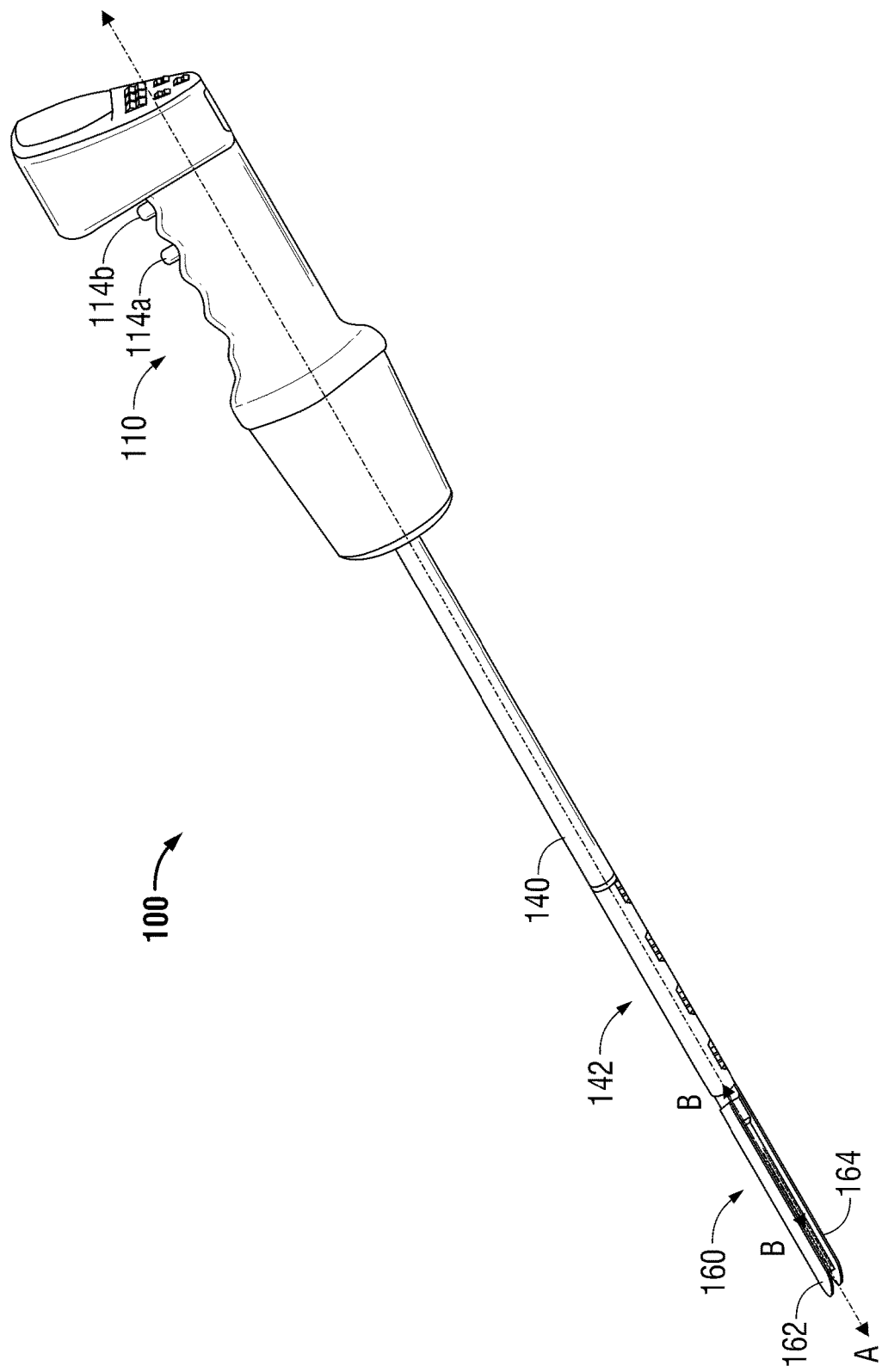
FIG. 1 is a perspective view of a powered surgical instrument according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of embodiments described herein.

A powered surgical instrument, e.g., a surgical stapler, in accordance with the present disclosure is referred to in the figures as reference numeral 100. Powered surgical instrument 100 is merely an example of a surgical instrument that utilizes the embodiments of the present disclosure described herein and therefore, is not intended to limit the present disclosure to this one particular embodiment of a surgical instrument.

Referring initially to FIG. 1, powered surgical instrument 100 includes a housing or handle 110, an endoscopic portion 140 defining a longitudinal axis A-A extending therethrough, and an end effector 160, defining a longitudinal axis B-B (illustrated substantially aligned with axis A-A in FIG. 1) extending therethrough. Endoscopic portion 140 extends distally from housing 110, and clamping mechanism or end effector 160 is disposed adjacent a distal portion 142 of endoscopic portion 140. End effector 160 is used to clamp, staple and/or cut tissue disposed therebetween.

Figure 2:
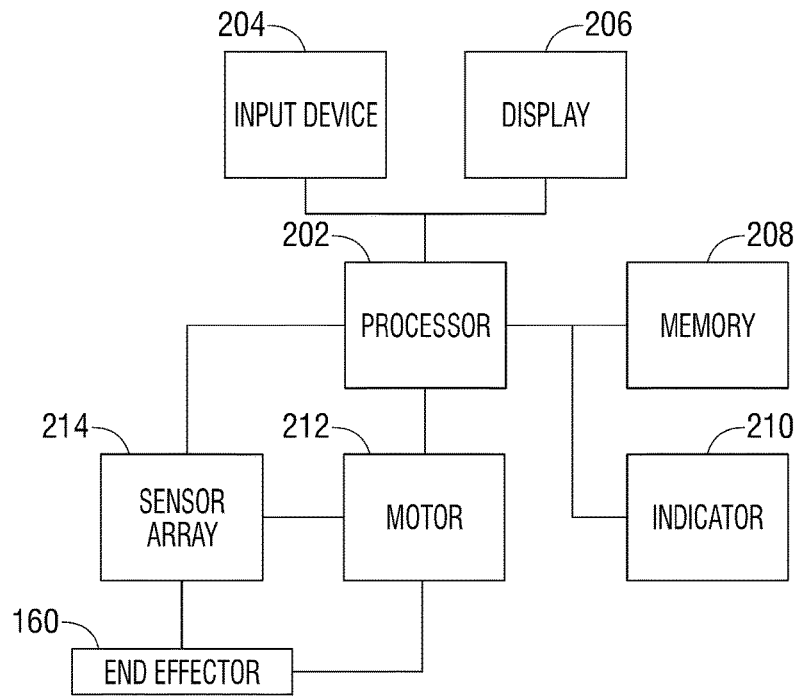
FIG. 2 is a system block diagram of the powered surgical instrument according to an embodiment of the present disclosure.

Powered surgical instrument 100 may include a control system designated generally as 200 in FIG. 2. Control system 200 may be integrated in housing 110 of powered surgical instrument 100 or some of the components may be provide in a stand-alone unit. Control system 200 includes a processor 202, an input device 204, a display 206, a memory 208, an indicator 210, a motor 212 and a sensor array 214.

Processor 202 may be an integrated circuit or may include analog and/or logic circuitry that may be used to: execute instructions according to inputs provided by the input device 204 or sensor array 214; execute instructions according to a program provided in memory 208; and/or control motor 212 thereby controlling the end effector 160 to clamp, staple and/or cut tissue therebetween.

Input device 204 may include a keyboard, a touchscreen input device, switches and/or buttons to control operation of the powered surgical instrument 100. Input device 204 may be used to: select between tissue management modes; control end effector 160; apply a staple or clamp; and input tissue properties such as tissue type and/or disease.

Display 206 may include a liquid crystal display, a light emitting diode display or the like. Display 206 may output a status of the powered surgical instrument, the measured tissue properties, the number of staples/clips applied, etc.

Control system 200 may also include an indicator 210 that may include at least one light emitting diode (LED) to indicate whether a tissue gap range, between the jaws of end effector 160, has been met. Indicator 210 may include a single multi-color LED or separate LEDs for red, yellow and green. The red LED may indicate a malfunction, a yellow LED may indicate that a tissue gap range has not been met and a green LED may indicate that the tissue gap range has been met. Additionally, an LED may be pulsed to indicate additional information. For instance, a pulsing yellow LED can indicate that an additional clamping cycle is being performed.

Sensor array 214 determines tissue properties by detecting the current draw on motor 212 or a dwell effect at end effector 160. The detected tissue properties are used to determine a clamping or tissue management mode, a tissue gap range, firing parameters, a speed of the motor, a modulation/pulse of the motor, deployment of the staples, etc. The tissue properties are used as an input to the iterative adjustment of the clamping pressure and duration for a tissue management mode.

Memory 208 may be a volatile type memory (e.g., RAM) and/or non-volatile type memory (e.g., flash media, disk media, etc.) that stores programs or sets of instructions for the operation of the powered surgical instrument 100.

Such programs include a number of tissue management modes that may be used to clamp tissue in order to apply a staple or clip to the tissue grasped by end effector 160. The tissue management modes are selected to apply an atraumatic stress or strain to the tissue by varying the compression of the tissue. The tissue management modes include a constant torque profile, a modulated torque profile, a maximum torque profile and a manual override mode. The tissue management modes may be automatically selected based on detected tissue parameters and/or tissue type and disease type inputted by a clinician or the tissue management mode may be selected by a clinician.

When a constant torque profile is selected, the powered surgical instrument 100 uses controlled tissue compression to apply constant rate if strain to tissue during the clamp, dwell and firing stages to optimize tissue gap and staple formation by applying a constant signal to motor 212 from processor 202. The parameters used to control the motor 212 and/or end effector 160 in the constant torque profile may be based on a desired speed of firing of the surgical instrument 100 or the type of tissue grasped by end effector 160.

The modulated torque profile applies pulsating or periodic strain energy to tissue by applying a periodic signal to motor 212. More specifically, processor 202 applies a pulse width modulated signal (PWM) or any other periodic signal to the motor to achieve an optimized compression profile, i.e., minimum tissue gap (maximum strain) with minimum tissue trauma (minimum stress). The optimized compression profile may vary for different tissue types and/or disease types. The signal from processor 202 may be predetermined and stored in a memory. Alternatively, the signal outputted by processor 202 may be determined by performing a current slope analysis on the current detected from the motor, initial tissue thickness $T_0$, initial clamped tissue thickness $T_1$ and total strain/energy.

When the tissue management mode is set for operation in the maximum torque profile, the surgical instrument 100 fires relatively faster than the other modes of operation. While in the maximum torque profile, surgical instrument 100 fires relatively faster at the beginning and at the end of the stroke where device stresses are relatively lower. When the tissue management mode is set to operate in the manual override mode, the clinician can manually control the motor of surgical instrument 100 to achieve the desired tissue gap of end effector 100 and to manually fire the surgical instrument 100.

Memory 208 may also store correlation tables to correlate tissue type and disease type to the requisite tissue gap range and firing parameters that need to be achieved to successfully apply a staple or clip to tissue.

Figure 3:
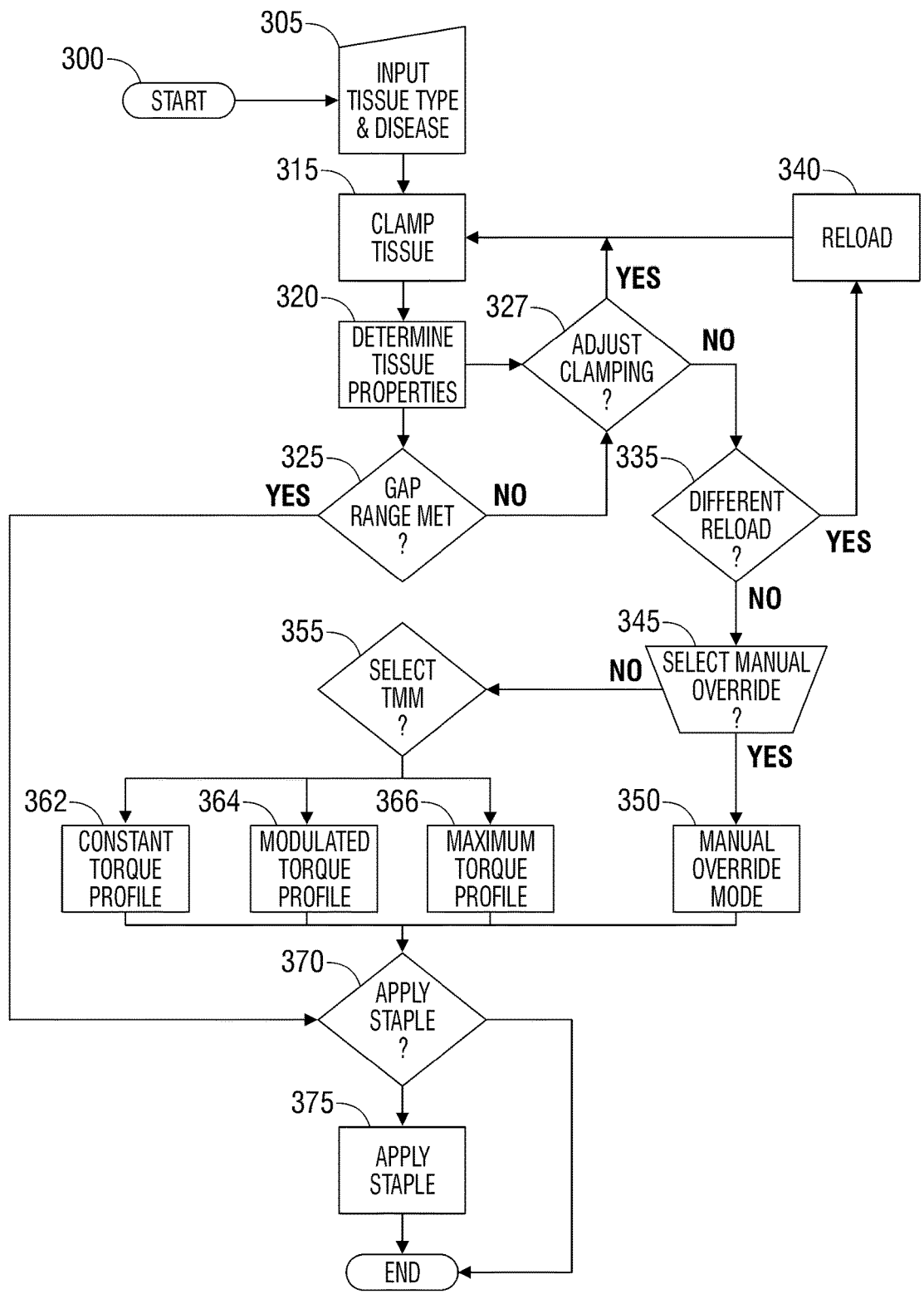
FIG. 3 is a flow chart depicting operation of the powered surgical instrument according to an embodiment of the present disclosure.

FIG. 3 depicts a flow chart describing an operation of the control system 200 of powered surgical instrument 100. As shown in FIG. 3, a clinician starts, "powers-up" or "turns on" the powered surgical instrument 100 in step 300. A clinician enters the tissue type and/or disease type in step 305 using input device 204. The clinician then positions end effector 160 onto the desired tissue and an initial clamping (tissue management) mode is determined. Then, in step 315, end effector 160 clamps the desired tissue and determines tissue propel lies such as initial thickness, density, initial clamped thickness, etc. in step 320. Processor 202, then, in step 325, determines if the tissue gap range is met for the particular tissue type. If the gap range is met, the control system 200 proceeds to step 370.

In step 325, if the gap range is not met, the tissue gap and tissue properties are evaluated by processor 202 to determine if additional clamping is beneficial. If it is, the gap range and tissue properties are used to determine a new clamping mode in step 327. The iterative clamping and evaluation process then returns to step 315 and is continued until an optimum gap range is met or it is determined that the tissue is unsuitable for the selected range in which instance the powered surgical instrument 100 prompts the clinician with a suggestion if a different reload or end effector (loaded with a different sized staple) should be used. If the clinician selects a different reload or end effector, then the powered surgical instrument 100 is reloaded in step 340 and proceeds to step 315 to clamp tissue.

If the clinician does not select a different reload or end effector, the clinician may select a manual override mode in step 345. If the user selects the manual override mode, the powered surgical instrument 100 is placed in the manual override mode in step 350.

Alternatively, the process proceeds to step 355 to select a tissue management mode. The tissue management mode may be automatically selected by processor 202 based on the inputted tissue type, disease type, and/or tissue propel lies or selected by the clinician. Based on the selection of the tissue management mode, the powered surgical instrument 100 may enter the constant torque profile of step 362, modulated torque profile of step 364 or the maximum torque profile of step 366. Then the control system 200 proceeds to step 370 where a determination is made as to whether a staple should be applied. This determination may be made by processor 202 or by the clinician. If the staple should be applied, then in step 375, the control system 200 controls the powered surgical instrument 100 to apply the staple. If the staple is not applied, the control system 200 ends the procedure (step 380) or restarts to apply a subsequent staple (step 300).

Figure 4:
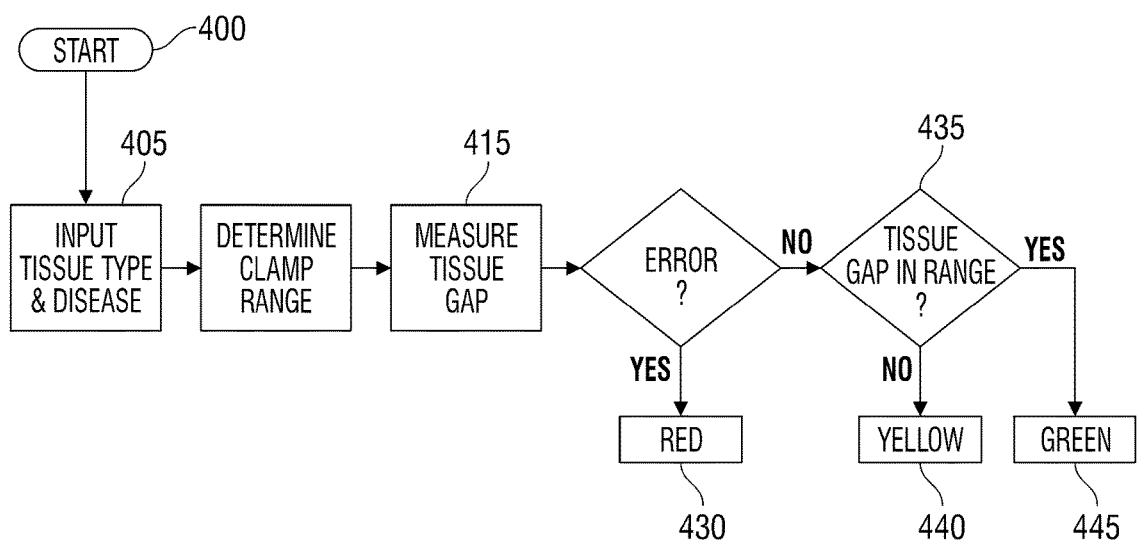
FIG. 4 is a flow chart depicting an indicator system according to an embodiment of the present disclosure.

FIG. 4 depicts a flow chart describing an operation of the indicator system of the powered surgical instrument 100. The powered surgical instrument 100 is started in step 400 and the tissue type and/or disease is entered in step 405. Processor 202 then uses one of the correlating tables stored in memory 208 to determine the tissue gap range for the red-yellow-green indicator 210. The tissue gap range is measured in step 415. If an error is determined or the tissue gap range exceeds an upper limit, the process proceeds to step 430 and the red indictor is illuminated. If there is no error or the tissue gap range does not exceed an upper limit, the process proceeds to step 435. If the tissue gap range is not in the acceptable range but it does not exceed the upper limit, the yellow indicator is illuminated in step 440. If the tissue gap range is met, the process proceeds to step 445 and the green indicator is illuminated.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A method of operating a powered surgical instrument, the method comprising:
   activating a motor of a surgical instrument, thereby clamping tissue with an end effector of the surgical instrument;
   determining at least one tissue property of the clamped tissue; and
   selecting a tissue management mode from a plurality of tissue management modes based on the determined at least one tissue property of the clamped tissue, the plurality of tissue management modes including a constant torque profile, a modulated torque profile, and a maximum torque profile, wherein the end effector is configured to apply a discrete strain on the clamped tissue in each of the plurality of tissue management modes, wherein in the modulated torque profile tissue management mode, the motor is configured to receive a pulse width modulated signal, thereby causing the end effector to apply a pulsating or periodic strain on the clamped tissue.

2. The method according to claim 1, further comprising activating the motor of the surgical instrument to apply the discrete strain on the clamped tissue by the end effector.

3. The method according to claim 2, wherein in the constant torque profile tissue management mode, the motor is configured to generate a constant torque.

4. The method according to claim 2, wherein in the maximum torque profile tissue management mode, the motor is configured to cause the end effector to clamp the tissue at a faster rate than in the constant and modulated torque profile tissue management modes.

5. The method according to claim 2, further comprising firing the surgical instrument to apply staples to the clamped tissue while the motor of the surgical instrument is operating in the selected tissue management mode.

6. The method according to claim 1, wherein the tissue management mode is selected automatically or by a clinician.

7. The method according to claim 1, further comprising determining whether a tissue gap of the end effector is within a tissue gap range.

8. The method according to claim 7, wherein the tissue management mode is selected after determining that the tissue gap of the end effector is within the tissue gap range.

9. The method according to claim 1, wherein the at least one tissue property of the clamped tissue includes a tissue type and a disease type.

10. The method according to claim 9, wherein the least one tissue property is determined by measuring a current draw on the motor.

11. The method according to claim 1, wherein the plurality of tissue management modes includes a manual override mode.

12. A method of operating a powered surgical instrument, the method comprising:

inputting at least one tissue property of tissue into a control system of a surgical instrument;

activating a motor of the surgical instrument, thereby clamping the tissue with an end effector of the surgical instrument; and selecting a tissue management mode from a plurality of tissue management modes based on the at least one tissue property of the clamped tissue, the plurality of tissue management modes including a constant torque profile, a modulated torque profile, and a maximum torque profile, wherein the end effector is configured to apply a discrete strain on the clamped tissue in each of the plurality of tissue management modes, wherein in the modulated torque profile tissue management mode, the motor is configured to receive a pulse width modulated signal, thereby causing the end effector to apply a pulsating or periodic strain on the clamped tissue.

13. The method according to claim 12, further comprising activating the motor of the surgical instrument to apply the discrete strain on the clamped tissue by the end effector.

14. The method according to claim 13, wherein in the constant torque profile tissue management mode, the motor is configured to generate a constant torque.

15. The method according to claim 13, wherein in the maximum torque profile tissue management mode, the motor is configured to cause the end effector to clamp the tissue at a faster rate than in the constant and modulated torque profile tissue management modes.

16. The method according to claim 13, further comprising firing the surgical instrument to apply staples to the clamped tissue while the motor of the surgical instrument is operating in the selected tissue management mode.

17. The method according to claim 12, further comprising determining whether a tissue gap of the end effector is within a tissue gap range.

18. The method according to claim 17, wherein the tissue management mode is selected after determining that the tissue gap of the end effector is within the tissue gap range.

* * * * *